United States Patent [19]

Stoy et al.

[11] 3,987,497

[45] Oct. 26, 1976

[54] TENDON PROSTHESIS

[75] Inventors: Artur Stoy; Miroslav Štol; Vladimír Stoy; Jiří Zima, all of Prague, Czechoslovakia

[73] Assignee: Ceskoslovenska akademie ved, Prague, Czechoslovakia

[22] Filed: Mar. 20, 1975

[21] Appl. No.: 560,215

[30] Foreign Application Priority Data

Mar. 29, 1974 Czechoslovakia .................. 2299-74

[52] U.S. Cl. .......................................... 3/1; 427/171
[51] Int. Cl.² ........................................... A61F 1/24
[58] Field of Search .................. 3/1, 1.9; 128/334 R

[56] References Cited
UNITED STATES PATENTS

| | | | |
|---|---|---|---|
| 3,176,316 | 4/1965 | Bodell | 3/1 |
| 3,220,960 | 11/1965 | Wichterle et al. | 3/1 X |
| 3,797,047 | 3/1974 | Pillet | 3/1 |
| 3,805,300 | 4/1974 | Tascon-Alonso et al. | 3/1 |
| 3,862,452 | 1/1975 | Wichterle et al. | 3/1 |
| 3,882,551 | 5/1975 | Helmer et al. | 3/1 |
| 3,931,123 | 1/1976 | Vacik et al. | 3/1 X |

*Primary Examiner*—Ronald L. Frinks

[57] ABSTRACT

The tendon prosthesis of the invention consists of a core formed of from a synthetic, preferably hydrophilic linear polymer oriented substantially in the direction of the main longitudinal axis of the prosthesis, having a tensile strength exceeding 100 kg/cm² and an elastic elongation of 8 – 50 percent, preferably 12 – 25 % of the resting length, and a sheath consisting of one or more layers of a hydrophilic, substantially nonoriented, physically or covalently crosslinked polymer with an equal or higher elastic elongation and an approximately equal or higher hydrophilicity than that of said core. The material of the core and particularly that of the sheath are permanently compatible with living tissue.

9 Claims, No Drawings

TENDON PROSTHESIS

BACKGROUND OF THE INVENTION

Replacement of tendons is a problem not yet satisfactorily solved because tendons derived from another individual are rejected. Sometimes a less necessary tendon from the same individual can be used, but this can hardly be considered an ideal solution. There was, until now, no synthetic material available possessing at the same time, physiological inertness, hydrophilicity and permeability for solutes together with high tenacity and elasticity. The usual synthetic filaments such as aromatic polyesters or polyamides possess, in a suitable arrangement of a set of twisted yarns good tenacity and elasticity, they are, however, impermeable for dissolved metabolites and irons; This property may increase the tendency towards some diseases, particularly if the size of the prosthesis is large. Synthetic hydrogels with proved compatibility with living tissues have usually a too low tensile strength.

According to the invention the tendon prosthesis consists of two parts with very different characteristics. The core bearing the load is formed from a mono-axially oriented linear polymer having the desired strength and a suitable elastic elongation of a value similar to that of a genuine tendon. The elastic elongation is obtained by imparting to the yarn a suitable twist. Instead of a yarn or cord a knitwork can be used, constructed in such a way that the average angle between individual filament and the load axis is less than 35°, as is twisted yarn. It is, however, possible to use hydrophilic linear polymers having sufficient elasticity as such, without any twist or knitting. Said modes can be combined, e.g. by using a fiber bundle having a genuine elastic elongation of 7 percent and twisting it so that the average angle of orientation is 12°, whereby an overall elastic elongation of 10.5 percent of the rest length is obtained.

Another way to obtain the desired overall elastic elongation is by using two materials: The central part of the core can be made from an elastic oriented hydrophilic polymer having a 20 percent elastic elongation while the outer layer of the core is a tubular knitwork made from a synthetic filament having a 1 percent elastic elongation, the individual filaments including with the load axis an average angle of 23°, Then, the core as a whole has a 20 percent elastic elongation.

Combinations of two or more materials of the core are advantageous because they make it possible to obtain desirable shape of the stress-strain curve, or that of the stress-modulus curve, with optimum characteristics from the view-point of the function of the prostheses. Such combinations also make possible a reliable fastening by means of a suture because the less elastic component protects the more elastic one against cutting through; moreover it makes it possible to fix the prosthesis not only by sewing but also by means of suitable adhesives, leaving the ends of the less elastic component such as the textile fabric or knitwork reinforcement protruding from the prosthesis. Oriented cords or yarns can protrude from one end or from both ends in the form of loops which can be easily fastened.

PREFERRED EMBODIMENT

Although various synthetic fibres and filaments twisted or knitted can be used such as polyamides, polyesters, polyurethanes, isotactic polyoefins such as polypropylene, polyacetates, polyvinyl chloride, vinyl chloride - vinylidene chloride copolymers, polyacrylonitrile and others, hydrophilic multiblock copolymers with acrylonitrile and acrylamide units alternating in long sequences are preferred. Such multiblock copolymers can be obtained by a controlled hydrolysis of polyacrylonitrile in an acid medium, e.g. in concentrated nitric acid, or in concentrated aqueous solutions of certain salts capable of dissolving polyacrylonitrile such as zinc chloride, gaseous hydrogen halide being used for accelerating the hydrolysis at low temperatures. Similar hydrophilic blockcopolymers can be obtained by partial controlled hydrolysis of polyvinyl acetate in a water-acetone solution, using basic catalysts, or chloromethylated polystyrene aminated by amino-alcohols. Other hydrophilic linear polymers useful in carrying out the invention are N-substituted polyamides, ternary copolyamides or copolyesters, hydrophilic polyurethanes, polyamides grafted with hydrophilic monomers such as methacrylic or acrylic acid etc. Most preferred however are multiblock copolymers of acrylonitrile with acrylamide obtained by the above mentioned partial acid hydrolysis of polyacrylonitrile, or similar multiblock copolymers of acrylonitrile with acrylic acid, obtainable by controlled partial saponification of polyacrylonitrile with strong alkalies in a homogeneous medium where the solvent or the swelling agent is a concentrated aqueous solution of a rohodanide, particularly of calcium or sodium rohodanide.

Said hydrophilic copolymers are very strong in oriented state, with a suitable elastic elongation up to 50 percent of the resting length and with a swelling capacity in water or in body liquids up to about 60 percent by weight, preferably between 20 and 45 percent.

The outer sheath of the prosthesis, consisting of non-oriented swelled hydrogel, protects the core against enzymes and other factors giving rise to deterioration. It can be made e.g. from a sparingly crosslinked 2-hydroxyethyl methacrylate polymer with usual swelling capacity of about 40 percent by weight, highly resistant to hydrolytic and other destruction agents. Moreover, the sheath envelops the core either as a whole or its individual strands, enhancing the strength and durability of the core. Enzymes and other biological factors with large molecules cannot penetrate through the gel. This is a big advantage because it is known that many synthetic fibers including polyethylene terephthalate and polyamides are gradually decomposed in a living body by enzymes such as esterases, amidases, urease and others.

The hydrophilic material of the core makes possible the transport of water and of aqueous solutions of lower-molecular substances. Therefore, the prosthesis is well tolerated. Moreover, the cross-linked gel shields the core against growing tissue which would otherwise immobilize the prosthesis. The sheath enables, moreover, the prosthesis to glide easily in the surrounding membranes and tissues. To this end, the surface of the sheath can be made extremely slippery by imparting anionic neutralized groups to it. Moreover, the hydrophilic polymer can be utilized for sustained drug release, facilitating the healing.

The above mentioned filamentous reinforcement protruding from the ends of the prosthesis and facilitating the fastening can be also covered by a hydrophilic polymer which can be, if desired, made macroporous so that collagen tissue can grow into it, improving the fastening of the prosthesis. In addition to using sutures, the ends of the prosthesis can be also cemented to the cartilage and bone by means of suitable adhesives such as butoxyethyl cyanacrylate. All above mentioned modes of fastening the prosthesis can be combined. The macroporosity of a chosen part of the protruding reinforcement covered by a cross-linked polymeric material can be obtained e.g. by polymerizing the monomers with an excess of water which is secluded in droplets during the polymerization, or by admixing soluble crystals to the monomer mixture and washing them out after the finished polymerization. When using the above mentioned multiblock copolymers of acrylamide with acrylonitrile strong elastic porous gels are obtained by admixing soluble crystals with the polymer solutions and washing them out during and after the coagulation. The pores should have an average diameter of more than 400 $\mu$ in order to open the way for growing collagen tissue fibres.

The sheath can be made from various hydrophilic polymers and copolymers. Besides the already mentioned sparingly crosslinked ethylene glycol methacrylate polymer and multiblock acrylonitrile - acrylamide copolymer it is possible to employ any other suitable hydrophilic polymer such as polymers and copolymers of monomethacrylates and acrylates of various polyols such as glycerol. diethylene glycol, 1,2-propylene glycol, 1,4-butylene glycol, pentaerythritol, with a small amount of the respective di- or trimethacrylates or -acrylates as crosslinking agents. Copolymers of acrylonitrile or methacrylonitrile with acrylamide or with N-substituted acryl- or methacrylamides can be also used, with or without crosslinking agents. If no crosslinking agent is used, the copolymer can be more easily shaped and in the final shape crosslinked subsequently using e.g. formaldehyde in an acid medium or other crosslinking agents such as diepoxides or di- and triisocyanates. Other suitable hydrophilic monomers are methacrylamide, vinyl pyrrolidone, vinyl pyridine. Crosslinking agents are added in a range of 0.05 to 3 percent /mol./. Examples of crosslinking agents are ethylene glycol dimethacrylate, glycerol trimethacrylate, divinyl sulfone, triacryloyl triazine, divinyl benzene or any other more-than G-functional compound, containing at least two polymeizable double bonds, or at least two three-membered epoxide or ethylene imino groups. Covalent crosslinking can be replaced or completed by physical crosslinking with strong non-covalent intermolecular bonds such as hydrogen bridges, nitrile dipoles, or ionic or coordination bonds.

The desirable hydrophilicity can be defined by following values: Insolubility in water, but in equilibrium with distilled water a water content at least 30 percent by weight at 20° C; Elastic elongation of the sheath material higher than about 50 percent of the resting length, the permanent elongation being negligible up to 50 percent total elongation.

The sheath can consist of several layers with characteristics differing according to the desired function. Thus, the interior layer designed to bind the components of the core together, can be made from a less hydrophilic and more crosslinked polymer, while the outer layer can be highly hydrophilic and less crosslinked, in order to reduce the irritation of the surrounding tissue by friction to a minimum. The outer layer can consist of a hydrogel containing neutralized anionic groups such as ethylene sulfonic groups, acid sulfuric groups, acid phosphoric groups or carboxylic groups or the like. To this purpose, copolymers of methacrylonitrile with sodium ethylene sulfonate or styrene sulfonate can be used, or the surface of the gel can be treated with glycerol and sulfuric acid, or with a strong alkaline lye, or with chlorosulfonic acid, with sulfur trioxide etc. , with subsequent neutralization and washing.

As far as the protruding textile reinforcement is designed to be fastened by leaving the collagen tissue to grow into it, or by cementing with cyanoalkyl acrylates or the like, the reinforcement is either left bare or covered with a layer of a macroporous polymer swellable in water. The same if the end of a tubular knitted reinforcement is designed to be sewn or cemented to a remainder of the original genuine tendon inserted thereinto.

The manufacture of the prosthesis of the invention can be carried out in several ways, depending on the sort of the material used and on the construction of the prosthesis. The core of the prosthesis can be made by extrusion of a solution or melt of the respective polymer into a coagulating bath or into the atmosphere respectively, using spinning nozzles with circular, oval or square holes. The filaments are oriented by stretching, advantageously prior to the removal of the last remainders of the solvent or prior to finished cooling of the melt.-spun filament. The filaments are then arranged e.g. in parallel bundles, or the core is formed from several such bundles which are twisted to an average angle less than 35 ° from the main longitudinal axis, or a tubular fabric or knitwork is made therefrom. Knitted or twisted filamentary reinforcement can be compounded with an elastic hydrphilic polymer in such a way that the reinforcement is compressed to an average angle to the longitudinal main axis larger than 35 ° and extruded together with the polymer solution into a coagulating bath. After having washed the solvent out from the gel, the whole is stretched so that the hydrophilic polymer is oriented to its optimum value and the reinforcement is simultaneously extended to its original resting length or to any other desirable length within its range of extensibility. Similarly, such compounded core can be made by dipping the appropriately compressed reinforcement into a polymer solution, coagulating the latter and then stretching to the pre-determinated length. Another possibility is to insert the filamentary reinforcement in compressed condition into a mold in which a monomer mixture is polymerized to an amorphous gel which is then stretched. Prior to stretching, the polymer can be transformed using a polymeranalogous reaction: For instance acrylonitrile can be polymerized in a mold filled with compressed reinforcement, in concentrated nitric acid. After the polymerization is finished, the polymer can be left at ambient or decreased temperature until a multiblockcopolymer of acrylonitrile with acrylamide is formed. Then the mold is dismantled, the reinforced gel washed in water to remove nitric acid, and hot stretched in a 70°– 100° C aqueous stretching bath, and cooled while stretched.

Still another possibility is to prepare a dispersion of powdered polyacrylonitrile in nitric acid cooled down to a temperature at which it cannot dissolve the polymer, and to pour the dispersion into a mold containing an appropriately compressed filamentary reinforcement under degassing. Upon gradually increasing the temperature, the dispersion turns to a clear viscous solution. The mold is then left at ambient or decreased temperature for a sufficient period of time until the desired degree of hydrolysis and the advantageous block-structure are achieved.

According to another method the hydrophilic non-oriented hydrogel is first oriented by stretching, and thereafter a tubular knitwork reinforcement is slid thereover and cemented, using an appropriate polymer solution, the solvent of which is a solvent or swelling agent for the oriented hydrogel. The solvent is then removed by evaporating or washing it out from the prosthesis. The polymer solution can form, after having been coagulated, the outer sheath, or a layer thereof.

An advantage of cores formed of an elastic oriented polymer an a substantially non-elastic oriented twisted or knitted polymer and surrounded by a non-oriented elastic gel is that filaments are not separated when subjected to repeated stress and the modulus plotted against the load is similar to that of a genuine tendon. The knitwork or twisted fibre bundles alone are elongated to the limit under a very low tension only, so that the modulus of the prosthesis is given substantially by the modulus of the elastic oriented core and that of the non-oriented crosslinked sheath, at least at low deformations. Separation of the filaments from the sheath under repeated load does not take place because the mutual position of individual fibres relative to the surrounding gel remains unchanged during the elongation.

The core is cut to a desired length prior to covering it with the sheath and the ends are adjusted for the intended mode of fastening. If the protruding ends of the filamentary reinforcement are to be provided with a layer of macroporous hydrogel, the latter can be joined with the reinforcement ends in a mold, using a mixture of a polymer solution with soluble crystals or particles. An additional reinforcement can be used to bind the two parts together.

The sheath on the core can be made e.g. by polymerization casting, or by dipping the core in a hydrogel solution, coagulating it, washing the solvent out from the coagulate and, if desired, by subsequent crosslinking as mentioned above.

The outer layer of the sheath can be made more hydrophilic than the inner one, either by forming a sequence of layers or by a chemical treatment of the surface. Besides the methods using agents capable of unparting anionic groups to the hydrogel, it is possible also to form the sheath from a lyogel consisting of polyacrylonitrile plasticized with a concentrated aqueous zinc chloride containing salt solution and treating said lyogel with gaseous hydrogen chloride from outside. The surface is exposed to the hydrolytic agent for a longer period of time than the interior and is therefore more hydrophilic. It contains also more carboxylic groups which make, in neutralized state, the surface more slippery.

As in the case of other implants, the washing, sterilizing and packaging is very important. The last washing can be carried out in physiologic saline in which the prosthesis is then kept. This last washing is preferably carried out in boiling saline at atmospheric or increased pressure so that the prosthesis is simultaneously sterilized. Appropriate drugs can be added if desired. The sterilization by boiling can be replaced or supplemented by chemical sterilization using e.g. ethylene oxide, or by irradiation with gammarays. In order to avoid relaxation of the oriented core it is necessary to clamp the prostheses, prior to boiling, in a suitable fixture which need not to be separated before packaging. The fixture makes possible another sterilization before use, if desired, e.g. if the package was damaged.

Several methods for manufacturing the tendon prostheses are disclosed in the following non-limitative Examples, wherein all percentages and amounts are by weight if not stated otherwise.

EXAMPLE 1

The oriented core was prepared by extruding a viscous solution of a multiblock acrylonitrile-acrylamide copolymer in nitric acid prepared in following way: 250 ml of acrylonitrile were dissolved in 750 ml of 65 percent nitric acid free of nitrogen oxides. The solution was stabilized by adding 1.3 g of urea dissolved in 2 ml of water, and initiated by adding 3.75 ml of a 5 percent aqueous solution of ammonium peroxodisulfate. The thoroughly stirred solution was kept for 72 hours at 20 °C in darkness and then in a refrigerator for 22 days at 7° – 8 °C. The solution was extruded using a die with 5 mm diameter. Coagulation bath was tap water 14 °C.

The thick monofil was coagulated, washed, neutralized and washed again in distilled water had a 4.5 mm diameter. It was oriented in a frame extended by screws in water at 75° – 80 °C for 2 hours. Its elastic elongation at a 2 – 3 kp/mm$^2$ load was 15 percent of the resting length. Its cross-section /unloaded/ was 8 mm$^2$, tensile strength higher than 12 kg/mm$^2$, the total tensile strength thus higher than 96 kp.

One or more of the swelled oriented monofilaments was then inserted into a knitted hose formed from oriented polyethylene terephthalate endless filament yarn fitting tightly to the hydrogel. if more than one hydrogel monofilament was used, the hose was fixed thereto by sewing it to the hydrogel monofilaments with a thread formed from the same polyester. The whole was then provided with a crosslinked smooth sheath by coating it with a viscous solution of soluble polyethyleneglycol methacrylate copolymer with 1 mol.percent of ethyleneglycol dimethacrylate in a monomer mixture, consisting of 50 percent pure glycerol, 49.5 percent 2-hydroxyethyl methacrylate and 0.2 percent of ethyleneglycol dimethacrylate, initiated with 0.3 percent of diethyl percarbonate. The coating was made in several layers, degassed and heated in inert gas to 60° – 70 °C, whereby the mixture polymerized to a transparent hydrogel.

The prosthesis could be cut to any desired length, sewn at any place with a polyester suture, if desired using simultaneously a cyanoacrylate adhesive.

EXAMPLE 2

A polyester silk knitwork with 25 percent elongation was rolled up forming a cylindrical roll of an about 5 mm diameter and fixed by stitching with a polyester thread. The roll was then inserted into a glass tube, the latter immersed with one end into a monomer mixture consisting of 70 percent 2-hydroxyethyl methacrylate, 0.25 percent ethyleneglycol dimethacrylate, 0.25 percent diethyl percarbonate and 29.5 percent boiled and cooled distilled water. The other end of the glass tube was connected with a water jet pump by means of a rubber tube and the monomer mixture was slowly sucked into the glass tube, the air trapped between fibres escaping into the pump. Then both ends of the glass tube were tightly closed with silicone rubber stoppers and the tube was immersed for one hour into a 65 °C warm water bath. The finished core was then pulled out from the cooled tube and provided with a sheath formed from a similar hydrogel: A viscous solution of a non-crosslinked copolymer of 2-hydroxyethyl methacrylate with 0.8 percent ethyleneglycol dimethacrylate in 2-hydroxyethyl methacrylate monomer containing 0.3 percent of ethylene glycol dimethacrylate as a crosslinking agent and 0.1 percent diethyl percarbonate as initiator for the polymerization was prepared and the core was dipped into it. After removal of the excessive solution by permitting the same drip off the coated core was hung underneath a lid which was, together with the core, screwed onto a tall flask filled with carbon dioxide heated to 60 ° C. After the crosslinking polymerization was finished the core was again dipped into said monomer solution, this time upside down in order to compensate for the uneven thickness caused by the monomer mixture flowing down. The new coating was again polymerized. The prosthesis thus obtained had the core formed by oriented polyethylene terephthalate knitwork embedded in the hydrogel, and a sheath formed by similar chemically stable sparingly crosslinked hydrogel, which was well tolerated by the living body. The rolled knitwork could be fastened using a suture combined with butoxycyanoacrylate adhesive.

EXAMPLE 3

Example 2 was repeated with a monomer mixture consisting of 70 percent 2-hydroxyethyl methacrylate, 0.4 percent of ethyleneglycol dimethacrylate, 29.8 percent oxygen-free distilled water, 0.1 percent potassium pyrosulfite and 0.1 percent ammonium peroxodisulfate. The monomer mixture cooled to 5 ° C was immediately after adding the peroxodisulfate sucked into a polyethylene tube with the rolled polyester knitwork therein and left standing at ambient temperature for 2 hours. After cutting the tube along its length the core was further treated as in the foregoing Example.

EXAMPLE 4

A water-swollen filament tow consisting of an acrylonitrile-acryamide multiblock- copolymer in the form of 110 filaments 50 denier each, having in swelled condition 20 percent elastic elongation and tensile strength 2100 $kg/cm^2$ at a water content of 19 percent at swelling equilibrium was pulled into a polyester knitted hose and the whole introduced into a glass tube, and flushed with carbon dioxide. Then the tube was filled with monomer mixture in the manner described in Example 2. The monomer mixture consisted of 5 volume parts of methacrylic acid, 5 Volume parts of 2-hydroxyethyl methacrylate, 5 volume parts of anhydrous acrylonitrile, 0.03 volume parts of ethyleneglycol dimethacrylate, 3 volume parts of water, 0.5 volume parts of a 5 percent aqueous solution of potassium pyrosylfite, 0.5 volume parts of a 5 percent aqueous solution of ammonium peroxodisulfate and 0.03 vol. parts of a 0.1% aqueous solution of cupric chloride dihydrate. The mixture was prepared by cooling externally to 0° – 5 ° C. The monomer mixture copolymerized at ambient temperature within 2 hours to a tough hydrogel. The core thus obtained was pulled out from the glass tube and washed thoroughly first in water and then in a diluted aqueous solution of potassium acetate. Onto the core an elastic hydrogel tube, swollen in aqueous dimethylsulfoxide 1:1 and consisting of a multiblock acrylonitrile-acrylamide copolymer obtained by low-temperature partial hydrolysis of polyacrylonitrile in 65 percent nitric acid according to Example 1 was slipped. The tube was prepared by extruding the copolymer solution in nitric acid through a die with an axial mandrel through which water was led in. The diameter of the circular extrusion die was 6 mm. The prosthesis was then put aside for 2 hours and washed in water until the solvent was fully removed. The non-oriented hydrogel tubular sheath was cemented with the core with dimethyl sulfoxide prior to the removal thereof by washing. The prosthesis was sterilized with ethylene oxide and sealed into a polyethylene foil filled with sterilized physiologic saline.

EXAMPLE 5

Polyethylene terephthalate cord 800 denier, twisted to an elastic elongation of 5 – 6 percent of the resting length, was fed by a pair of gears at a rate of 48 cm/min into a central tube of an extrusion die with 8 mm outer diameter through which a solution of partly hydrolyzed polyacrylonitrile in 65 percent nitric acid was extruded at a rate of 10 cm/min. The coagulating bath was diluted nitric acid. About 6 mm thick monofil having a polyester cord inserted therein was obtained. After a thorough washing in water to neutral reaction the monofilament was stretched in 85 ° C water until the cord inside the gel was almost straightened. In the stretching bath 1 percent of formaldehyde and 0.5 percent of concentrated hydrochloric acid had been previously dissolved so that the stretched hydrogel was sparingly crosslinked. If the core was elongated elastically to 20 percent of its resting length, the cord was extended tight increasing the strength of the prosthesis. A polyester knitted hose, tightly fitting to the core, was then slid on and the whole was polymerized in a silicone rubber tube into a monomer mixture consisting of 99.5 percent of 2-hydroxyethyl methacrylate, 0.3 percent ethyleneglycol dimethacrylate and 0.2 percent diisopropyl percarbonate at 60 ° C. The prosthesis was sterilized with ethylene oxide and swelled to equilibrium in physiologic saline in a sterile packing.

EXAMPLE 6

Non-oriented endless filament from polyethylene terephthalate was twisted and combined in a 2000 den tow so as not to stretch them permanently. The tow was then pulled through an extrusion nozzle, extruding smultaneously a copolymer solution in nitric acid according to Example 1. The coagulated, neutralized and washed strand was then oriented by stretching in 98 ° C hot water to 520 percent of the resting length. The cooled core had an elastic elongation of 20 percent, at which the polyester tow was fully stretched; in relaxed core the polyester filaments were slightly curled to 83.3 percent of the stretched length. A polyester knitted hose was slid on and the whole was polymerized into sparingly crosslinked 2-hydroxyethyl methacrylate polymer like in Example 5.

EXAMPLE 7

Example 6 was repeated with the difference that instead of the copolymer solution in nitric acid a similar solution in aqueous zinc chloride solution was used. The solution was prepared by polymerizing 12 percent of anhydrous acrylonitrile in 88 percent of a mixture of 3 volume parts of a 70 percent aqueous zinc chloride solution and 2 volume parts of an aqueous calcium chloride solution saturated at ambient temperature. The solution was cooled to 5 ° C and initiated with 0.15 percent potassium pyrosulfite and the same amount of ammonium peroxodisulfate, related to the monomer. The polymerization was carried out without stirring and cooling and lasted about 20 minutes. The viscous solution thus obtained was extruded through a 1 mm diameter spinning nozzle into a 1 m tall flask filled with a mixture of 80 volume percent of air and 20 vol. percent of hydrogen chloride. As soon as a 50 mm layer of the solution accumulated on the bottom, the solution was slowly drawn off at the same rate as introduced through the spinneret so that the level in the flask remained unchanged. Samples were taken at one hour intervals until the coagulated gel, thoroghly washed, displayed 40 – 45 percent swelling water content. The bulk of the solution was degassed and extruded together with the unoriented tow into an excess 0.5 percent sodium hydrocarbonate solution. After removing entirely zinc chloride so that no further precipitate was formed the core was washed in distilled water, stretched and treated as in Example 6.

Alternatively, the copolymer was spun first into diluted sodium hydrocarbonate solution, washed and dissolved in either dimethyl formamide or dimethyl sulfoxide and then extruded together with the unoriented polyester tow etc.

In the preceding disclosure as well as in the following claims, the term "linear polymer" is to be understood in contradistinction of "crosslinked polymer", involving thus branched polymers and copolymers, especially those with long branches which are, from the practical standpoint, almost identical in their behavior with strictly linear polymers.

We claim:

1. Tendon prosthesis consisting of a core and of a sheath, the core consisting essentially of a linear polymer oriented predominantly in the direction of the main axis of the prosthesis and having a tensile strength of at least 100 kg/cm$^2$ the core as a whole having an elastic elongation in the range of between 8 and 50 percent, of its resting length, the sheath consisting of at least one layer of a substantially non-oriented hydrophilic polymer which is crosslinked and has an elastic elongation at least equal to and a water swelling capacity at least equal to said core.

2. Tendon prosthesis according to claim 1, wherein the oriented linear polymer of the core is hydrophilic having at least 15 percent swelling capacity in water.

3. Tendon prosthesis according to claim 1, wherein the oriented linear polymer core comprises filaments embedded in an unoriented hydrogel.

4. Tendon prosthesis according to claim 1, wherein a part of the core forms a filamentary reinforcement.

5. Tendon prosthesis according to claim 4, wherein the filamentary reinforcement comprises a knitwork having an elastic elongation approximately equal to that of the other components of the core.

6. Tendon prothesis according to claim 1, characterized in that the core protrudes at the ends from the sheath.

7. Tendon prosthesis according to claim 4, characterized in that the filamentary reinforcement protrudes from the ends.

8. Tendon prosthesis according to claim 1, characterized in that said sheath consists of a sparingly crosslinked 2-hydroxyethyl methacrylate polymer.

9. Tendon prosthesis according to claim 1, characterized in that said core consists of oriented linear polymer filaments embedded in an oriented hydrogel.

* * * * *